United States Patent
Akai et al.

(10) Patent No.: US 9,805,468 B2
(45) Date of Patent: Oct. 31, 2017

(54) SAMPLE IMAGE MANAGEMENT SYSTEM AND SAMPLE IMAGE MANAGEMENT PROGRAM

(71) Applicant: DAI NIPPON PRINTING CO., LTD., Shinjuku-ku, Tokyo (JP)

(72) Inventors: Tomonori Akai, Tokyo (JP); Masanori Kagota, Tokyo (JP); Takuma Baba, Tokyo (JP)

(73) Assignee: DAI NIPPON PRINTING CO., LTD., Shinjuku-ku, Tokyo (JP)

(*) Notice: Subject to any disclaimer, the term of this patent is extended or adjusted under 35 U.S.C. 154(b) by 88 days.

(21) Appl. No.: 14/917,704

(22) PCT Filed: Aug. 21, 2014

(86) PCT No.: PCT/JP2014/071870
§ 371 (c)(1),
(2) Date: Apr. 27, 2016

(87) PCT Pub. No.: WO2015/037406
PCT Pub. Date: Mar. 19, 2015

(65) Prior Publication Data
US 2016/0239957 A1  Aug. 18, 2016

(30) Foreign Application Priority Data
Sep. 11, 2013  (JP) ................................. 2013-188247

(51) Int. Cl.
*G06T 7/00* (2017.01)
*C12M 3/00* (2006.01)
(Continued)

(52) U.S. Cl.
CPC .......... *G06T 7/0012* (2013.01); *C12M 21/06* (2013.01); *C12M 23/12* (2013.01); *C12M 41/00* (2013.01);
(Continued)

(58) Field of Classification Search
CPC .......... G06K 9/00127; G06K 9/00134; G06K 9/0014; G06T 7/0012; G06T 7/70;
(Continued)

(56) References Cited

U.S. PATENT DOCUMENTS

| | | | |
|---|---|---|---|
| 7,963,906 B2 * | 6/2011 | Wong et al. | 600/33 |
| 2010/0221768 A1 | 9/2010 | Akai et al. | 435/29 |
| 2015/0243014 A1 * | 8/2015 | Bise et al. | G06T 7/0004 382/110 |

FOREIGN PATENT DOCUMENTS

| | | | | |
|---|---|---|---|---|
| EP | 1691196 A1 | 8/2006 | | G01N 33/53 |
| JP | 4724854 B2 | 7/2011 | | C12M 1/00 |

(Continued)

OTHER PUBLICATIONS

Supplementary European Search Report for Corresponding European Application No. EP 14844020.9 (dated May 2, 2017).

*Primary Examiner* — Andrew W Johns
(74) *Attorney, Agent, or Firm* — Lucas & Mercanti, LLP

(57) ABSTRACT

Provided is a sample image management system that uses a cell culture vessel including a plurality of microwells and a plurality of first identifiers provided to the respective microwells in pairs. The sample image management system analyzes, in an enlarged sample image including a pair of the first identifier and the microwell, the microwell and the first identifier, and associates at least position information on the microwell with the enlarged sample image.

15 Claims, 11 Drawing Sheets

| Well ID | Angle α | ... |
|---|---|---|
| A | 45 | ... |
| B | 90 | ... |
| C | 135 | ... |
| ⋮ | ⋮ | ⋮ |

(51) Int. Cl.
  *C12M 1/32*  (2006.01)
  *C12M 1/34*  (2006.01)
  *G06F 19/00* (2011.01)
  *G06K 9/00*  (2006.01)
  *G06K 9/46*  (2006.01)

(52) U.S. Cl.
  CPC ............ *C12M 41/36* (2013.01); *C12M 41/46* (2013.01); *G06F 19/366* (2013.01); *G06K 9/00134* (2013.01); *G06K 9/00147* (2013.01); *G06K 9/46* (2013.01); *G06T 2207/10056* (2013.01); *G06T 2207/30024* (2013.01)

(58) Field of Classification Search
  CPC . G06T 7/74; G06T 2207/30024; G06F 19/36; G06F 19/366; C12M 23/12; C12M 23/50; C12M 41/48; G01N 35/00732; G01N 2035/00742; G01N 2035/00772; G01N 2035/00821; G01N 2035/00831
  See application file for complete search history.

(56) References Cited

FOREIGN PATENT DOCUMENTS

| | | | | |
|---|---|---|---|---|
| WO | 2009123748 A1 | 10/2009 | ............... | C12Q 1/02 |
| WO | 2011047044 A2 | 4/2011  | ............. | C12N 15/87 |
| WO | 2012047678 A2 | 4/2012  | ............. | A61B 10/02 |
| WO | 2014121205 A1 | 8/2014  | ............. | G01N 33/48 |

* cited by examiner

| Vessel Number | Second Identifier Information | ... |
|---|---|---|
| 1 | 0123 | ... |
| 2 | 0124 | ... |
| 3 | 0125 | ... |
| ⋮ | ⋮ | ⋮ |

1101, 1102

| Image ID | Vessel Number | Well ID | Image Data |
|---|---|---|---|
| 123456 | 1 | A | |
| 123457 | 1 | B | |
| | | | |
| | | | |

1201, 1202, 1203, 1204

Enlarged Sample Image → Contour Extracted Image

Orientation of First Identifier

Corrected Image

SAMPLE IMAGE MANAGEMENT SYSTEM AND SAMPLE IMAGE MANAGEMENT PROGRAM

CROSS-REFERENCE TO RELATED APPLICATIONS

This application is a 371 of PCT/JP2014/071870, filed Aug. 21, 2014, which claims the benefit of Japanese Patent Application No. 2013-188247 filed Sep. 11, 2013.

TECHNICAL FIELD

The present invention relates to a system and a program for managing an enlarged sample image of a cell (i.e., a cell that should be managed individually, such as an embryo) in a cell culture vessel.

BACKGROUND ART

Embryos (zygotes) are produced by in vitro fertilization of sperm and oocytes in a culture system. The embryos are then cultured to a stage of hatched blastocysts having hatched from the zona pellucida via the stages of cleavage, morula, and then blastocyst. As a result of realization of these techniques, assisted reproductive technology (ART) has been established not only in the field of domestic animals, but also in the field of medical care for human infertility, which involves implantation of the embryos at a stage between cleavage and blastocyst into the uterus, no as to obtain infants.

However, in vitro fertilization does not always result in a high pregnancy success rate. For example, the pregnancy success rate of human in vitro fertilization still remains at a level of about 25% and 35%. A reason for this is the low possibility of obtaining high-quality embryos suitable for implantation into the uterus by culture. Whether or not cultured embryos are high-quality embryos suitable for implantation into the uterus is identified by specialists who observe each embryo via a microscope.

In in vitro fertilization, a microdrop method is often used where droplets of a culture solution are produced in a vessel, and embryos are put in the vessel to effect in vitro culture. Conventionally, in the microdrop method, a petri dish having a bottom surface with a single plane and with a diameter of 30 to 60 mm is used as a cull culture vessel, and a plurality of droplets of a culture solution are produced at intervals on the bottom surface of the petri dish, so that cells are cultured in the droplets.

When droplets are produced in an ordinary petri dish, the position of each embryo may change due to the cell movement of the embryo itself or due to convection that may occur within each droplet. Thus, it becomes difficult to identify embryos that have been cultured and observed in the petri dish, which is problematic. Thus, a means capable of controlling the positions of embryos has been demanded.

In order to increase the effect of culturing embryos more efficiently, it is preferable to use the interaction (i.e., paracrine effect) between embryos. In order to control the positions of embryos while using such effect, there is known a system for culturing embryos in which microwells with about the same size as embryos are formed at the bottom of a petri dish so that droplets of a culture solution are added covering the plurality of microwells, and then, the embryos are placed in the microwells filled with the culture solution. Accordingly, it becomes possible to individually observe a plurality of embryos while controlling the positions thereof, and culture a plurality of embryos in a small amount of culture solution while using the paracrine effect.

Meanwhile, in order to distinguish between individual embryos, it is necessary to identify individual microwells. Since microwells are observed with a microscope, it is necessary to estimate as many pieces of information as possible only from the field of the microscope. However, if the magnification is high, it is impossible to determine which microwell is currently viewed. Thus, in order to identify individual micro-wells, there is known a method of adding information, such as numbers or characters, to the outer periphery of a microwell array so that the microwells can be identified in a matrix manner.

However, when a microwell is observed with a microscope at high magnification using the above method, it is necessary to read the identification information by greatly shifting the observation position from the current microwell, which is problematic in terms of workability. Further, when a cell is imaged with a microscope, it is necessary to manually provide information to the obtained photograph data, which involves complex work, as the photograph does not originally contain the identification information on the microwell. Furthermore, there is a possibility that the operator may make a mistake in the process of associating the information with the photograph data.

CITATION LIST

Patent Literature

Patent Literature 1: JP 4724854 B

SUMMARY OF INVENTION

Technical Problem

It is an object of the present invention to provide a sample image management system and program that uses a cell culture vessel having a plurality of microwells, the system and program being capable of associating, from an enlarged image of a microwell, the position of the microwell with the enlarged image.

Solution to Problem

The inventors have found that the aforementioned problems can be solved by, in a cell culture vessel having a plurality of microwells and a plurality of first identifiers provided to the respective microwells in pairs, acquiring an enlarged sample image including a pair of a first identifier and a microwell, and analyzing the microwell and the first identifier in the enlarged sample image.

That is, the present invention includes the following.

(1) A sample image management system including:

a cell culture vessel including a plurality of microwells and a plurality of first identifiers provided to the respective microwells in pairs;

a storage unit that stores first information, the first information including position information on each microwell and information on each first identifier that are associated with one another; and a sample image management unit that analyzes, in an enlarged sample image including a pair of the first identifier and the microwell, the microwell and the first identifier, and associates at least the position information on the microwell in the first information with the enlarged sample image on the basis of the first information.

(2) The sample image management system according to (1), in which the cell culture vessel further includes a second identifier, and the sample image management unit associates the second identifier read from the cell culture vessel and the position information on the microwell in the first information with the enlarged sample image.

(3) The sample image management system according to (1) or (2), in which the sample image management unit, in analyzing the microwell and the first identifier in the enlarged sample image, extracts an outer contour of the microwell and a contour of the first identifier in the enlarged sample image.

(4) The sample image management system according to any one of (1) to (3), in which the sample image management unit, in analyzing the microwell and the first identifier in the enlarged sample image, analyzes an orientation of the first identifier in the enlarged sample image, and corrects the enlarged sample image by rotating the enlarged sample image.

(5) The sample image management system according to any one of (1) to (4), in which the information on the first identifier in the first information includes at least one of information on a relative position of the first identifier with respect to its paired microwell, and information held by the first identifier, and the sample image management unit, in analyzing the microwell and the first identifier in the enlarged sample image, recognizes at least one of the relative position of the first identifier with respect to its paired microwell or the information held by the first identifier in the enlarged sample image (6) A program for causing an information processing device, which includes at least a processor and a storage unit, to execute a sample image management process for a cell culture vessel that includes a plurality of microwells and a plurality of first identifiers provided to the respective microwells in pairs, the program causing the processor to execute:

a process of analyzing, in an enlarged sample image including a pair of the first identifier and the microwell, the microwell and the first identifier; and a process of associating, on the basis of first information, which includes position information on the microwell and information on the first identifier that are associated with one another, at least the position information on the microwell in the first information with the enlarged sample image.

(7) The program according to (6), in which the cell culture vessel further includes a second identifier, and the program further causing the processor to execute a process of associating the second identifier read from the cell culture vessel and the position information on the microwell in the first information with the enlarged sample image.

(8) The program according to (6) or (7), in which the analyzing process includes extracting an outer contour of the microwell and a contour of the first identifier in the enlarged sample image.

(9) The program according to any one of (6) to (8), in which the analyzing process includes analyzing an orientation of the first identifier in the enlarged sample image and correcting the enlarged sample image by rotating the enlarged sample image.

(10) The program according to any one of (6) to (9), in which the information on the first identifier in the first information includes at least one of information on a relative position of the first identifier with respect to its pair microwell, and information held by the first identifier, and the analyzing process includes recognizing at least one of the relative position of the first identifier with respect to its paired microwell, and the information held by the first identifier in the enlarged sample image.

Advantageous Effects of Invention

According to the present invention, with a cell culture vessel having a plurality of microwells, it is possible to associate, from an enlarged image of a microwell, the position of the microwell with the enlarged image.

Further features related to the present invention will become apparent from the description of the specification and the accompanying drawings. In addition, problems, configurations, and advantageous effects other than those described above will become apparent from the following description of embodiments.

DESCRIPTION OF EMBODIMENTS

Figure 1:
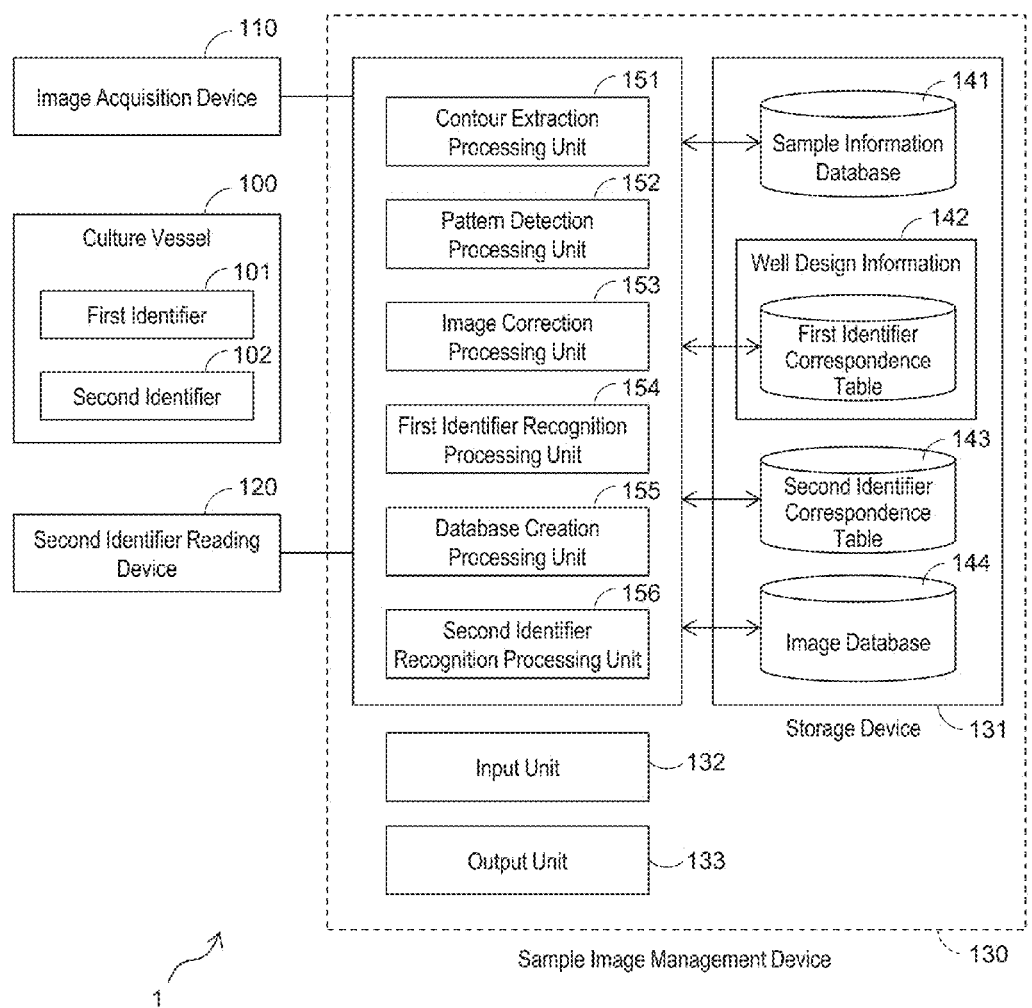
FIG. 1 is a configuration diagram of an embodiment of a sample image management system of the present invention.

Hereinafter, the present invent on will be described. FIG. 1 is a configuration diagram of an embodiment of a sample image management system of the present invention. A sample image management system 1 includes a cell culture vessel 100, an image acquisition device 110, a second identifier reading device 120, and a sample image management device 130. Hereinafter, each component of the sample image management system 1 will be described.

Figure 2:
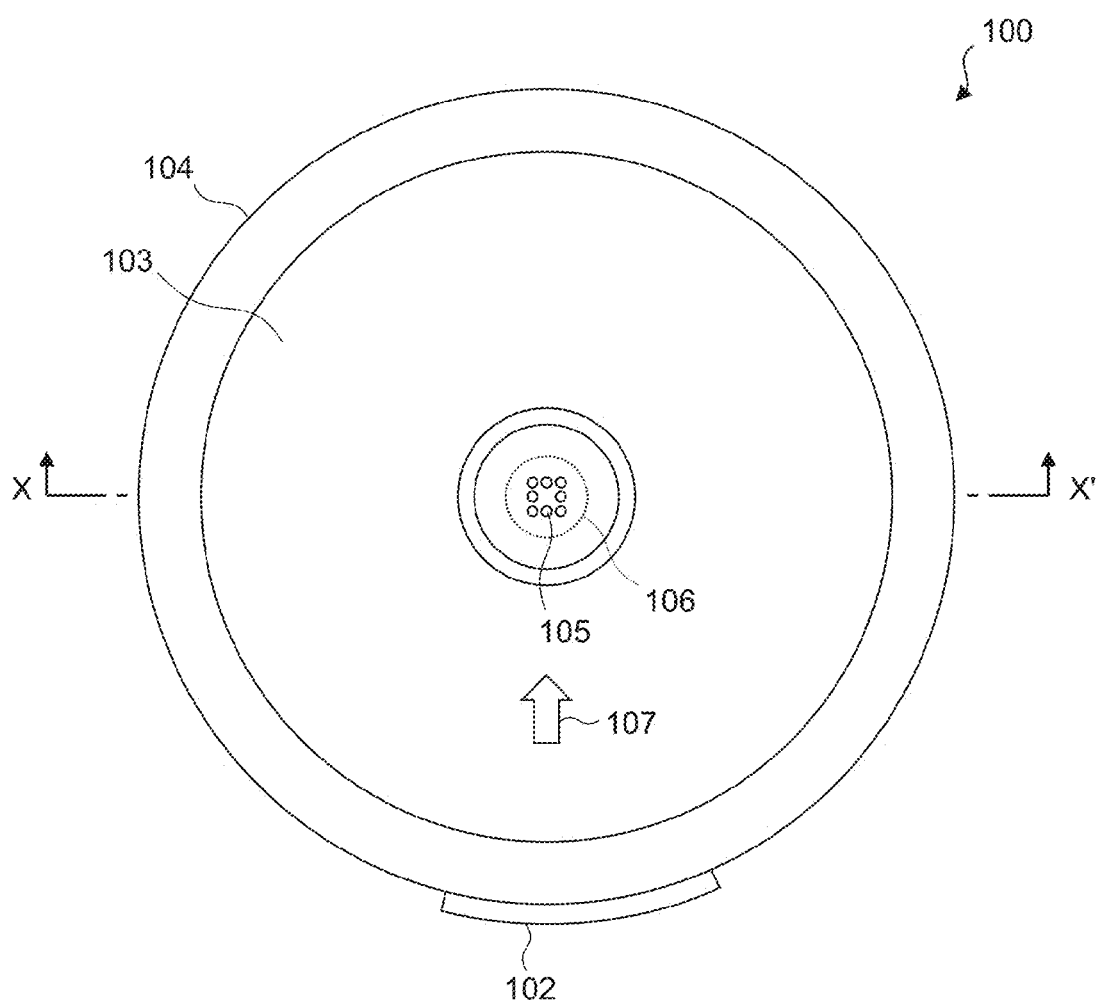
FIG. 2 is a schematic diagram showing a top view of an embodiment of a cell culture vessel of the present invention.
Figure 3:
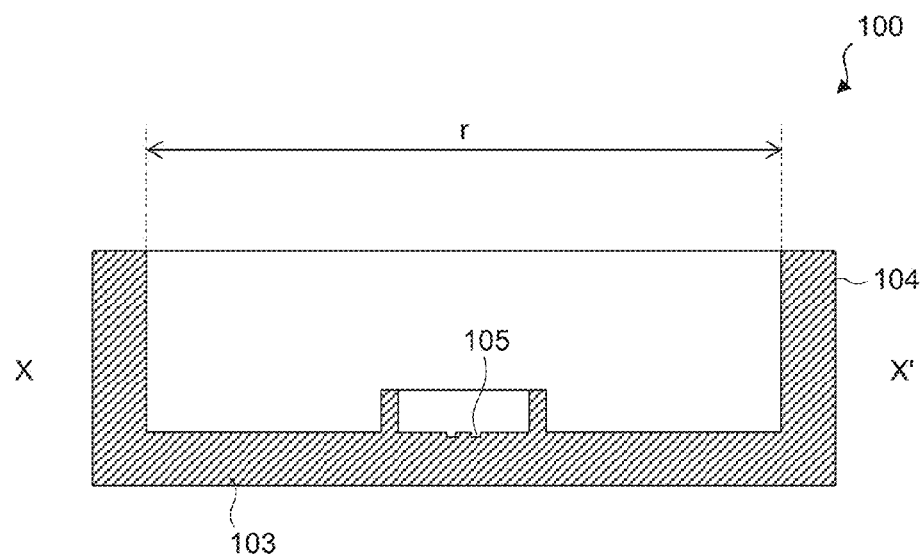
FIG. 3 is a schematic diagram showing a vertical sectional view of an embodiment of the cell culture vessel of the present invention.

As shown in FIG. 1, the cell culture vessel 100 includes a first identifier 101 and a second identifier 102. FIGS. 2 and 3 each show a specific configuration of the cell culture vessel 100. The cell culture vessel 100 in this embodiment has a bottom 103 and a sidewall 104, and the bottom 103 has a cell storage part 106 having disposed thereon a plurality of microwells 105 for storing cells. The shape of the bottom 103 is not particularly limited, and may be polygonal, such as triangular or quadrangular, or circular (including circular, approximately circular, elliptical, and approximately elliptical shapes). The sidewall 104 is formed on as to cover the outer rim of the bottom 103.

A side opposite to the bottom 103 is usual y open, and the shape of the opening is preferably identical to that of the bottom 103. Preferably, a cell culture vessel having a circular opening with an opening width (r in FIG. 3, for example) of preferably 30 to 60 mm and, in particular, 35 mm, is used. This is the same size as that of the conventional petri dish used for culturing cells. Thus, such a size is preferable as the cell culture vessel can be easily produced from the general-purpose petri dish, and can be easily adapted to the existing culture device and the like. It should be noted that the cell culture vessel 100 may have a lid like those of the ordinary petri dishes.

Figure 4:
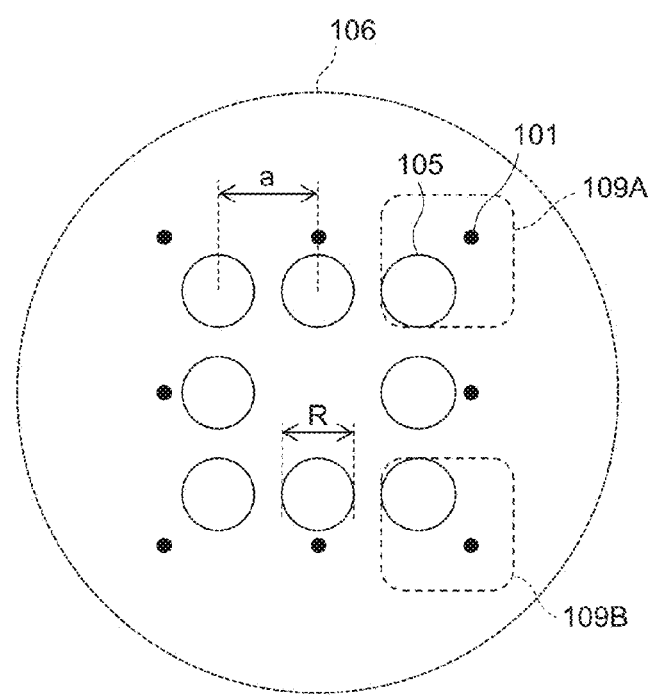
FIG. 4 is a schematic diagram showing an enlarged top view of a cell storage part of an embodiment of the cell culture vessel of the present invention.
Figure 5:
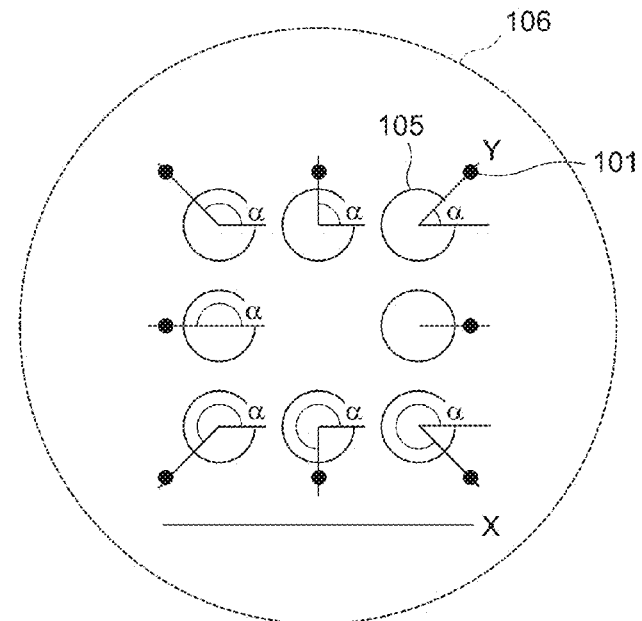
FIG. 5 is a schematic diagram showing an enlarged top view of a cell storage part of an embodiment of the cell culture vessel of the present invention.

FIGS. 4 and 5 are schematic diagrams each showing an enlarged top view of a cell storage part of an embodiment of the cell culture vessel of the present invention. First identifiers 101 are provided around the plurality of microwells 105 in pairs. The present invention is characterized in that the relative position of the first identifier 101 with respect to its corresponding microwell 105 differs from pair to pair. As the relative position of the first identifier 101 with respect to its corresponding microwell 105 differs for each microwell 105, it is possible to identify the position of a microwell among the plurality of microwells 105 only by observing a pair of the microwell 105 and the first identifier 101. As the first identifier 101 is provided around each microwell 105, observation at high magnification can be performed quickly without the need to greatly shift the observation position from the current microwell 105. Further, even when a cell is imaged at high magnification, the obtained enlarged sample image includes the first identifier 101 as well as the microwell 105. Thus, there is no need to manually provide information to the enlarged sample image. Therefore, complex work can be avoided, and a risk of errors, which may occur due to an operator's failure in associating information with the enlarged sample image, can be avoided.

Each microwell 105 preferably has formed therein a recess that is suitable for individually storing a cell, such as an embryo, and the size of the recess is very small. The present invention is characterized in that a very small first identifier 101 is provided to each of such very small microwells 105. Specifically, the area of the opening of each microwell 105 seen in the top view of the cell culture vessel 100 is preferably less than or equal to 3 $mm^2$, or more preferably less than or equal to 1 $mm^2$, or further preferably less than or equal to 0.5 $mm^2$, and is preferably greater than or equal to 0.03 $mm^2$.

Each microwell 105 has formed therein a recess that has a wall surface and an opening. Such a recess may be a recess that is provided directly as a dent in the bottom 103 of the cell culture vessel 100, or a recess that is formed by a member projecting from the bottom 103. That is, the area of the opening of each microwell 105 seen in the top view is the area of a figure that is formed by the outer rim of the opening of the microwell 105. The figure formed by the outer rim of the opening of the microwell 105 is not particularly limited, and may be polygonal, such as triangular or quadrangular, or circular (including circular, approximately circular, elliptical, and approximately elliptical shapes). However, the figure is preferably circular. When the outer rim of the opening of the microwell 105 is circular, the opening width is equal to the diameter of the circle (R in FIG. 4), which is greater than the maximum dimension of a cell that is cultured.

When the outer rim of the opening of each microwell 105 is circular, the opening width is narrower than the pitch between the microwells 105. Thus, the opening width of the opening of each microwell 105 (or if the outer rim of the opening of the microwell 105 is circular, the diameter of the circle) is preferably greater than or equal to 0.1 mm, or more preferably greater than or equal to 0.15 mm, or further preferably greater than or equal to 0.2 mm, and is preferably less than 0.6 mm, or further preferably less than 0.4 mm. In addition, the opening width of the opening of each microwell 105 can also be defined as X+m (where X represents the maximum diameter of a cell). Herein, m is preferably greater than or equal to 0.01 mm, or further preferably greater than or equal to 0.02 mm.

The number of the microwells 105 that are arranged on the bottom 103 of the cell culture vessel 100 of the present invention is preferably greater than or equal to 4, or further preferably greater than or equal to 8, for example, greater than or equal to 10, and is preferably less than or equal to 50, or more preferably less than or equal to 30. Thus, cells, such as embryos, can be placed in the microwells 105 one by one, so that a plurality of cells can be cultured.

The pitch between the microwells 105 is preferably less than or equal to 1 mm, more preferably less than or equal to 0.8 mm, or further preferably less than or equal to 0.6 mm. As the image acquisition device 110, a device that has a ½-inch CCD device and 4×, 10×, and 20× objective lenses is often used. The field of view that can be observed with the 4× objective lens selected with such an image acquisition device 110 is about 1.6 mm×1.2 mm. The image acquisition device 110 in such a case is preferably designed so t at the observed field of view contains greater than or equal to 4 microwells 105.

The pitch between the microwells 105 is the distance between the centers of the neighboring microwells 105 (a in FIG. 4, for example). The center of each microwell 105 is the center of gravity of a figure that is formed by the outer rim of the opening of the microwell and is, if the outer rim is circular, the center of the circle. The pitch between the microwells 105 usually indicates the average pitch, and the average pitch indicates the average value calculated from the pitches of all of the neighboring microwells 105. The pitch between the microwells 105 is greater than the dimension of the outer rim of the opening of each microwell 105. The dimension of the outer rim of the opening of each microwell 105 indicates, if the outer rim of the opening is circular, the diameter of the circle, or otherwise, indicates the minimum diameter of a figure that is formed by the outer rim of the opening.

The plurality of the neighboring microwells 105 are preferably arranged in a tetragonal lattice or in a closest packed structure. For example, 25 microwells can be arranged in a tetragonal lattice of 5×5 microwells. When the microwells 105 are arranged in a tetragonal lattice or in a closest packed structure, it becomes further easier to identify the position of each microwell 105 at the bottom 103 of the cell culture vessel 100 from a combination of the microwell 105 and the first identifier 101. Thus, such an arrangement can be easily applied to an automated process. In addition, if information on the pitch between the microwells 105 and the like are registered in advance as the well design information, it becomes possible to, when the observed field of view contains a plurality of microwells 105, use the information to perform a process of cutting out each pair of the microwell 105 and the first identifier 101.

The plurality of microwells 105 may also be arranged in a tetragonal lattice or a closest packed structure with a partially missing structure. For example, a case is considered where greater than or equal to 8 microwells are arranged at an equal pitch on the sides and the vertices of a parallelogram, thus forming a cell storage part. Examples of a parallelogram include a square, a rectangle, a rhombus, and other parallelograms. A case where the microwells 105 are arranged on the sides and the vertices of a parallelogram means that the center of gravity of a figure that is formed by the outer rim of the opening of each microwell 105 is arranged on the side or the vertex of the parallelogram. For example, in the embodiment shown in FIG. 4, 8 microwells are arranged on the four vertices as well as on the midpoints of the four sides of a square one by one.

The first identifier 101 that is provided in a pair with each microwell 105 may be arranged either inside or outside the microwell 105, but is preferably arranged outside the microwell 105. This is because if the first identifier 101 is provided inside the microwell 105, it may disturb the observation of an embryo or influence the culture performance of an embryo. Preferably, the first identifier 101 is provided in the gap between adjacent microwells 105 of the plurality of microwells 105 arranged as above. Thus, the first identifier 101 is small enough to be arranged in such a gap. The size of the first identifier 101 is preferably smaller than that of each microwell 105. Thus, the size of the first identifier 101 is, in the top view of the cell culture vessel 100, preferably within the size of a figure that is formed by the opening of each microwell 105. More specifically, the area of the first identifier 101 in the top view of the cell culture vessel 100 is less than or equal to 30,000 $\mu m^2$, or preferably less than or equal to 15,000 $\mu m^2$, or more preferably less than or equal to 8,000 $\mu m^2$, and is preferably greater than or equal to 100 $\mu m^2$.

In addition, the first identifier 101 is provided at a position sufficiently close to its corresponding microwell 105 on that which microwell 105 is paired with the first identifier 101 can easily identified. Thus, each first identifier 101 is preferably provided so that the distance between the first identifier 101 and its corresponding microwell 105 of all the microwells 105 becomes the shortest. The distance between each first identifier 101 and its corresponding microwell 105 is defined as the distance between the center of gravity of a figure that is formed by the opening of the microwell 105 and the center of gravity of a figure that is formed by the first identifier 101. Thus, the distance between each first identifier 101 and its corresponding microwell 105 is preferably greater than half the opening width of the microwell 105 and smaller than the pitch between the microwells 105. Specifically, the distance between each first identifier 101 and the microwell 105 is less than or equal to 500 $\mu m$, or more preferably less than or equal to 400 $\mu m$, or further preferably less than or equal to 300 $\mu m$.

The first identifiers 101 are preferably provided to all microwells 105 in the cell storage part 106. However, even if there are some microwells 105 that are not provided with the first identifiers 101 (for example, at a percentage of less than or equal to 10% of the total number of microwells that are included in the cell storage part 106), such a configuration is included in the present invention. This is because if there are some microwells 105 in which no cells are stored and thus are not the targets to be observed, such microwells 105 need no first identifier 101. The first identifiers 101 are preferably provided to the microwells 105 in a one-to-one correspondence. However, it is also possible to provide two or more identifies to one microwell 105.

The shape of each first identifier 101, that is, the shape of a figure that is formed by each first identifier 101 is not particularly limited. Examples of figures include figures, such as characters, numbers, or polygons; arrows; lines (bars); dots; QR codes (registered trademark); barcodes, and a combination of them. The shape of the first identifier 101 is preferably a simple shape that can be easily formed because the first identifier that is preferably smaller than the very small microwell 105, which is suitable for storing a cell, such as an embryo, is provided around the microwell 105. This is because as the cell culture vessel 100 is often produced through injection molding, it is difficult to mold the cell culture vessel 100 in a too complex shape and in a very small size. Even when the shape of the first identifier 101 is simple, that is, even when the amount of information held by the first identifier 101 is small, it is possible to identify the position of each microwell 105 by adding information, such as the relative position of the first identifier 101 with respect to the microwell 105. If the first identifier 101 is formed in a complex shape, there is a possibility that yields in the production of the cell culture vessel 100 may decrease. However, if the first identifier 101 is formed in a simple shape, it is possible to avoid a decrease in yields and reduce the production cost.

Therefore, each first identifier 101 is preferably in the shape of a dot or a line (bar). FIGS. 4 and 5 show examples of the dot-like first identifiers 101. In the examples herein, 8 microwells 105 are arranged on the four vertices as well as on the midpoints of the four sides of a square one by one, thus forming the cell storage part 106. In addition, the dot-like first identifiers 101 are provided around the microwells 105 one by one. The present invention is characterized in that the relative position of each first identifier 101 with respect to its corresponding microwell 105 differs for each pair of the first identifier 101 and the microwell 105.

A configuration in which the relative position of the first identifier 101 with respect to its corresponding microwell 105 differs for each pair of the first identifier 101 and the microwell 105 includes a configuration in which the distance between the first identifier 101 and its corresponding microwell 105 differs from pair to pair and a configuration in which the angle of the first identifier 101 with respect to its corresponding microwell 105 differs from pair to pair.

The distance between each first identifier and its corresponding microwell 105 is as described above. The angle α of each first identifier with respect to its corresponding microwell 105 can be defined as follows. For example, in the embodiment shown in FIGS. 4 and 5, the angle α can be defined as, when a straight line X is drawn on the bottom 103 of the cell culture vessel 100 in the top view, an angle made by a straight line that is parallel with the straight line X and a straight line Y that passes through the center of gravity of the microwell 105 and the center of gravity of the first identifier 101 (FIG. 5). When the first identifiers are arranged such that the angle α between the microwell 105 and the first identifier 101 differs from pair to pair, it is possible to identify the position of a specific microwell 105 among the plurality of microwells 105. It is also possible to increase the amount of information by combining the distance and the angle. In this embodiment, as the angle α of the first identifier 101 with respect to its corresponding microwell 105 differs from pair to pair, it is possible to identify the position of each microwell 105 only by observing a pair of the microwell 105 and the first identifier 101.

Figure 6:
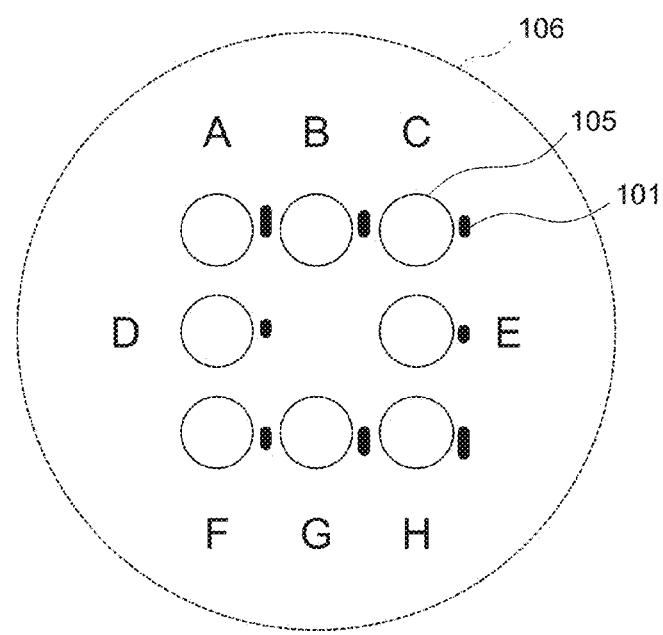
FIG. 6 is a schematic diagram showing an enlarged top view of a cell storage part of an embodiment of the cell culture vessel of the present invention.
Figure 7:
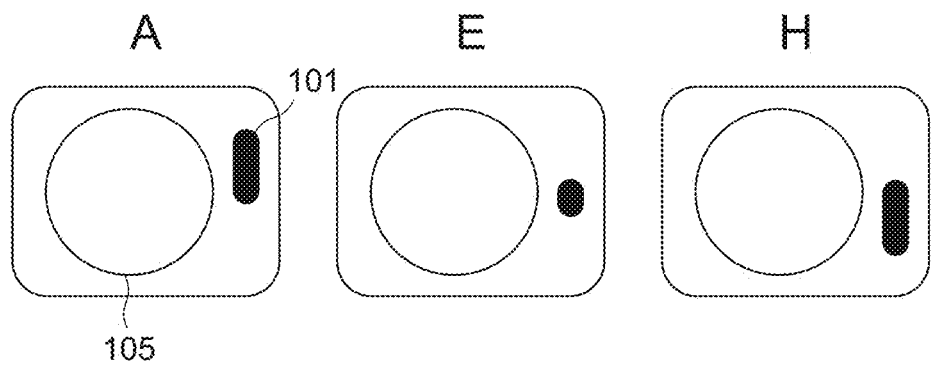
FIG. 7 is a conceptual view of an enlarged image of a pair of a microwell and an identifier captured with a microscope.

FIGS. 6 and 7 show examples of the linear first identifiers 101. In the examples herein, 8 microwells 105 are arranged on the four vertices as well as on the midpoints of the four sides of a square one by one, thus forming the cell storage part 106. In addition, the linear identifiers 101 are provided around the microwells 105 one by one.

FIG. 7 represents a microscope image of a pair of the microwell 105 and the first identifier 101 at each of positions A, E, and H in FIG. 6. In this embodiment, the distance between the first identifier 101 and the microwell 105 of each pair is substantially the same. However, as the angle α of the first identifier 101 with respect to its corresponding microwell 105 and/or the length of the line (bar) differ(s) from pair to pair, it is possible to identify the position of each microwell 105 only by observing a pair of the microwell 105 and the first identifier 101. Further, as all of the first identifiers 101 are in the shapes of lines that are oriented in the same direction, and are provided to the right of the respective microwells 105, it is possible to identify, even from an enlarged image of a pair of a microwell 105 and a first identifier 101 captured at high magnification, the orientation of the cell culture vessel at the time of capturing the image based on the position of the first identifier 101 and the orientation of the line (bar). The "orientation" herein is the angle of rotation, and differs from the angle α. For example, when each dot in the embodiment shown in FIG. 4 is replaced by a line (bar), the "orientation" indicates the angle of rotation of the line with respect to the straight line X at the position of the dot, that is, the angle made by the straight line X and the line of the identifier. Using the volume of information on the orientation can identify the orientation of the culture vessel. Further, varying the orientation of each first identifier 101 can also increase the amount of information held by the first identifier 101.

It should be noted that a single cell culture vessel 100 and a single cell storage part 106 may have both the dot-like first identifiers 101 and the linear first identifiers 101 in a mixed manner. Providing both of such first identifiers can increase the amount of information. Further, varying the length of each of the linear first identifiers 101 can also increase the amount of information held by the first identifier 101.

There may be cases where a plurality of first identifiers 101 that are provided to a plurality of microwells 105 one by one are preferably arranged coaxially. The plurality of microwells 105 herein need not be all of the microwells 105 in the cell storage part 106, and indicate a plurality of microwells whose centers of gravity are coaxial, preferably greater than or equal to 2 microwells, or more preferably greater than or equal to 3 microwells, or further preferably greater than or equal to 4 microwells. If a plurality of first identifiers 101, which are provided to the respective microwells 105 whose centers of gravity are coaxial, are arranged coaxially, it is possible to, when switching the microwell 105 to be observed during the high-magnification observation, grasp a pair of the microwell 105 and its corresponding first identifier 101 only by moving the cell culture vessel 100 relative to the lens in the X-axis direction or in the Y-axis direction. Thus, quick observation is possible.

Further, as the field of view in the microscope observation is typically horizontally long, it is possible to observe a plurality of first identifiers 101, which are arranged along the horizontal axis, at a time. In addition, when the long-side direction of the field of the microscope is aligned with the axial direction of the first identifiers 101, it is possible to observe all of the first identifiers 101 even in the high-magnification observation. This is particularly advantageous when the short-side distance of the field of view is quite close to the diameter of each micro-well 105, for example. A configuration in which a plurality of first identifiers 101 are arranged coaxially does not mean that the centers of gravity of the first identifiers 101 are arranged exactly coaxially, but small deviations are acceptable as long as high-magnification observation can be performed quickly.

Next, the second identifier 102 will be described. The cell culture vessel 100 is provided with the second identifier 102. Examples of the second identifiers 102 include figures, such as characters, numbers, or polygons; QR codes (registered trademark); barcodes; IC tags; dot patterns (coded patterns); and a combination of them. Herein, the technique of a dot pattern (coded pattern) will be briefly described. A dot pattern is printed on the surface of dedicated paper for electronic pens, for example. The dot pattern has a combination of 6×6=36 dots that are arranged in a lattice pattern at intervals of about 0.3 mm. 6 (vertical)×6 (horizontal) dots are arranged such that a unique pattern is seen from any 6×6 dots on the dedicated paper. The dot pattern formed by such 36 dots holds its position coordinates (which indicate the position on the dedicated paper at which the dot pattern is located, for example) and a dot pattern address that is an identifier unique to each dedicated paper. Each dot is associated with predetermined information in accordance with the shift direction from the reference position of the lattice. That is, with this technique, it is possible to allow a dot pattern to correspond to the second identifier 102 by allowing the shift direction of each dot from the reference position of the lattice to correspond to a character, number, or the like. The dot pattern can be imaged using a reading means, such as an electronic pen, with a built-in camera. The technique of the dot pattern described herein is also described in JP 2004-252607 A and JP 2004-054375 A. Thus, the techniques described in such documents can be used. The second identifier 102 may also be provided to the sidewall 104 or the bottom 103 of the cell culture vessel 100. If the cell culture vessel 100 has a lid, the second identifier 102 may also be provided to the lid. The second identifier 102 differs for each cell culture vessel 100. Thus, recognizing the second identifier 102 can identify the cell culture vessel 100.

When a pair of the microwell 105 and the first identifier 101 is repeatedly imaged at high magnification to obtain a plurality of pairs, it is necessary to set the orientation of the cell culture vessel 100 to be always constant during the imaging process. Otherwise, the tilt of the cell culture vessel 100 may be included in the angle α, in which case, it is impossible to distinguish the relative position from the tilt on an enlarged image even though the relative position actually differs on t e cc vessel 100.

Figure 8:
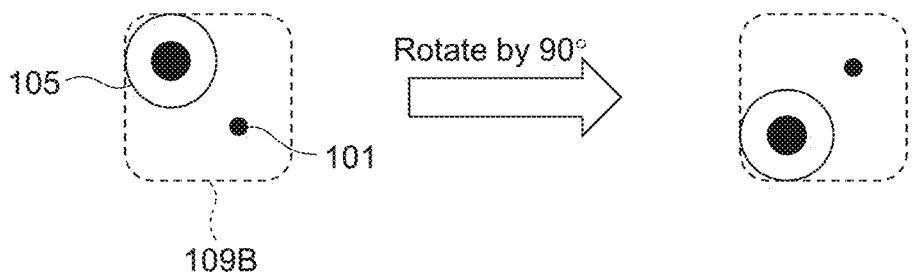
FIG. 8 is a conceptual view of an enlarged image of a pair of a microwell and an identifier captured with a microscope.

For example, referring to the enlarged view of the cell storage part 106 shown in FIG. 4, it is impossible to distinguish between an enlarged image of a pair 109A of a microwell 105 and a first identifier 101 arranged at the upper right vertex and an enlarged image of a pair 109B of a microwell 105 and a first identifier 101 arranged at the lower right vertex of FIG. 4 that has been captured by rotating the cell culture vessel 100 to the left by 90° from the state shown in FIG. 4 (FIG. 8). From a perspective of setting the orientation of the cell culture vessel 100 to be always constant during the imaging process, the cell culture vessel 100 is preferably provided with a third identifier for identifying the orientation of the cell culture vessel 100 besides the first identifier 101 and the second identifier 102.

The third identifier is preferably a visible identifier as it is used in capturing an enlarged sample image. Therefore, in the top view of the cell culture vessel 100, the area of the third identifier is preferably larger than the area of the opening of each microwell 105. The third identifier is preferably provided on the bottom 103 and outside the cell storage part 106 that has the plurality of microwells 105 arranged therein (for example, reference numeral 107 in FIG. 2). The third identifier may also be provided on the sidewall 104 of the cell culture vessel 100. Alternatively, the orientation of the cell culture vessel may be set always constant by the shape of the cell culture vessel 100 itself. That is, when the outer periphery of the sidewall 104 of the cell culture vessel 100 is formed in a shape that can identify the orientation of the cell culture vessel 100, for example, a partially missing circular shape, it is possible to set the orientation of the cell culture vessel 100 to be always constant during the imaging process. In such a case, the shape of the cell culture vessel 100 is not particularly limited as long as the orientation of the cell culture vessel can be identified.

Alternatively, if each first identifier 101 has a linear shape, it has two-dimensional information unlike a case where the first identifier 101 has a dot shape. Thus, even without the third identifier, it is possible to identify the orientation of the cell culture vessel to a certain degree on an enlarged image of a pair of a microwell 105 and a first identifier 101 captured at high magnification. That is, if all of the first identifiers 101 are formed in the shapes of lines that are oriented in the same direction on the top view of the cell culture vessel 100, it is possible to identify the orientation of the cell culture vessel during the imaging process to a certain degree even on an enlarged image of a pair of a microwell 105 and a first identifier 101 captured at high magnification, based on the orientation of the line (bar).

Further, if the first identifiers 101 are provided to only the right side, only the left side, only the upper side, or only the lower side of the plurality of microwells 105 in the cell storage part 106, it is also possible to identify the orientation of the cell culture vessel 100 on an enlarged image of a pair of a microwell 105 and a first identifier 100 captured at high magnification. As the general position of the first identifier 101 is determined in advance for each target microwell 105 to a certain degree, it is possible to easily determine the imaging position when manually imaging an embryo at high magnification. Further, in such a configuration, a process of correcting an enlarged image through rotation can also be automated as described below.

Herein, the right side, the left side, the upper side, and the lower side of a microwell can be defined as regions that are obtained by dividing a region of the microwell around the center of gravity thereof (360°) into four. For example, a region where a shown in FIG. 5 is in the range of 45 to 135° can be defined as the upper side. Thus, even when identifiers are provided to only the upper side of microwells, it is possible to vary the relative positions of the identifiers with respect to their corresponding microwells within such orange.

Next, other components of the sample image management system 1 will be described. The image acquisition device 110 is adapted to capture an enlarged sample image that includes a cell in the microwell 105 of the cell culture vessel 100 and the first identifier 101 and is, for example, a microscope. As the image acquisition device 110, a device that has a ½-inch CCD device and 4×, 10×, and 20× objective lenses is often used.

The second identifier reading device 120 is a device that reads the second identifier 102 of the cell culture vessel 100. As the second identifier reading device 120, a device that corresponds to the second identifiers 102 may be adopted. For example, a known character/figure recognition device, a camera, a barcode scanner, or an IC tag reader can be used.

The sample image management device 130 includes an information processing device, such as a personal computer or a workstation. The information processing device includes a processor, such as a CPU (Central Processing Unit), a storage device 131, such as a memory or a hard disk, an input unit 132, such as a keyboard or a mouse, and an output unit 133, such as a display. Although FIG. 1 shows the sample image management device 130 as a single information processing device, the present invention is not limited thereto. The components of the sample image management device 130 may be distributed as a plurality of information processing devices on a network. In addition, a variety of tables, databases, and the like may also be stored in other information processing devices or storage devices on the network.

Next, a variety of pieces of information used by the sample image management system 1 in this embodiment will be described. The storage device 131 has stored therein a sample information database 141, well design information 142, a second identifier correspondence table 143, and an image database 144. Although a variety of such tables and databases will be hereinafter described using "table" structures, such tables and databases need not be represented by data structures of tables, and may be represented by other data structures. Therefore, in order to show that such tables and databases do not depend on their data structures, they may be simply referred to as "information" hereinafter.

Figure 9:
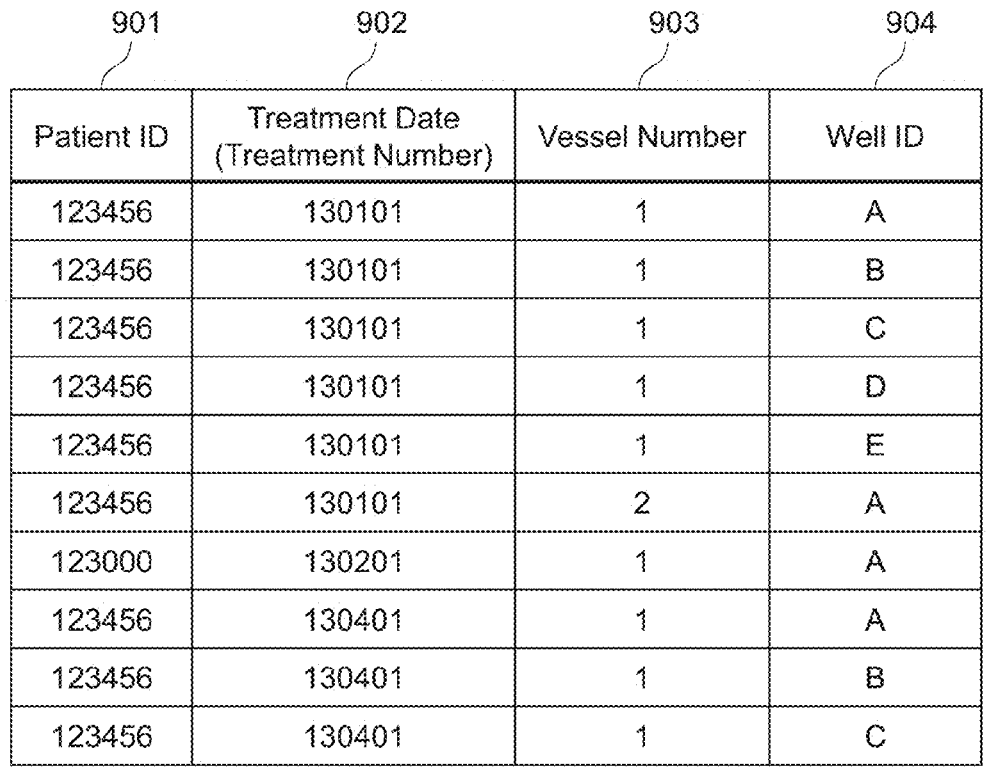
FIG. 9 is a schematic diagram showing an embodiment of a sample information database of the present invention.

FIG. 9 shows an example of the sample information database 141. The sample information database 141 has stored therein a variety of pieces of information on cells (i.e., cells that should be managed individually, such as embryos) in the cell culture vessel. The sample information database 141 contains a patient ID 901, a treatment date (i.e., treatment number) 902, a vessel number 903, and a well ID 904 as the constituent items. The patient ID 901 is a number for uniquely identifying a patient. The treatment date (i.e., treatment number) 902 is a number string indicating a treatment date. The vessel number 903 is a number for uniquely identifying the cell culture vessel 100. For example, there are cases where a plurality of cell culture vessels are used for the same patient ID and the same treatment date. In such cases, each cell culture vessel is managed by the vessel number 903. When a plurality of cell culture vessels are not used for the same patient ID or the same treatment date, the vessel number 903 may be omitted. The well ID 904 is an ID for identifying the position of each microwell 105 in the cell culture vessel 100. With the well ID 904, it is possible to manage information on a sample, such as a cell (e.g., embryo), put in the microwell 105.

Figure 10:
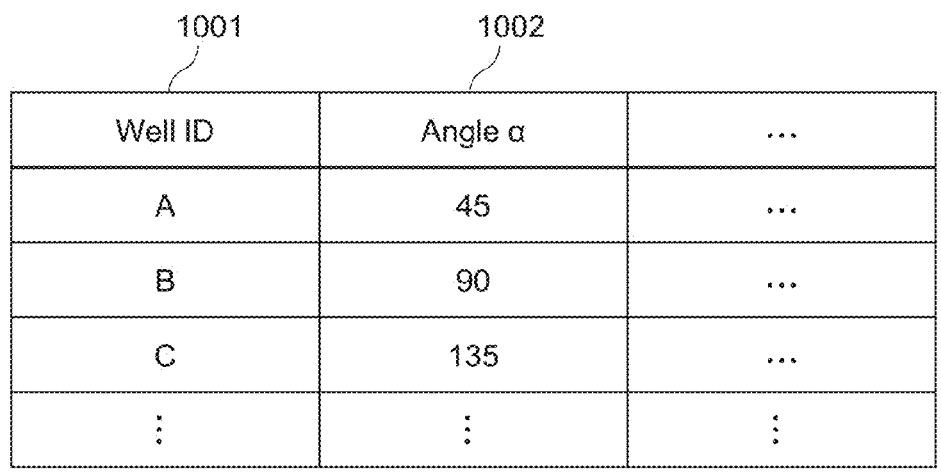
FIG. 10 is a schematic diagram showing an embodiment of a first identifier correspondence table of the present invention.

The well design information 142 includes at least a first identifier correspondence table. FIG. 10 shows an example of the first identifier correspondence table. The first identifier correspondence table contains at least a well ID 1001 and information 1002 indicating the relative position between the first identifier 101 and the micro-well 105 (herein, the angle α of the first identifier 101 with respect to the microwell 105) as the constituent items. Thus, the position (well ID 1001) of each microwell 105 can be identified only by observing a pair of the microwell 105 and the first identifier 101. Although the well ID 1001 is used as the position information on each microwell in this embodiment, the present invention is not limited thereto, and any other forms of information can be used as long as the position of each microwell can be identified.

It should be noted that in the first identifier correspondence table, the value of the angle α may be set with a predetermined margin as there is a possibility that errors may occur in the image processing of the sample image management device 130 described below. Although FIG. 10 shows only information on the angle α, if each first identifier 101 is a line (bar), it is also possible to store information indicating the relative position between the first identifier 101 and the microwell 105 (i.e., angle α) and/or information held by the first identifier 101 (i.e., length or orientation of the line). The first identifiers 101 may be figures, such as characters, numbers, or polygons; arrows; lines (bars); dots; QR codes (registered trademark); barcodes; or a combination of them, as described above. Thus, it is acceptable as long as the first identifier correspondence table stores information on the first identifiers corresponding thereto.

The well design information 142 may also include, in addition to the first identifier correspondence table, design information such as, for example, the shape of each microwell 105, the dimension of the outer rim of the opening of the microwell 105, the area of the opening of the microwell 105, and the pitch between microwells 105. In addition, the well design information 142 may also include design information on the first identifier 101 paired with each microwell 105. The design information on the first identifier 101 is information such as the shape, size, and position of the first identifier 101.

Figures 11, 12:
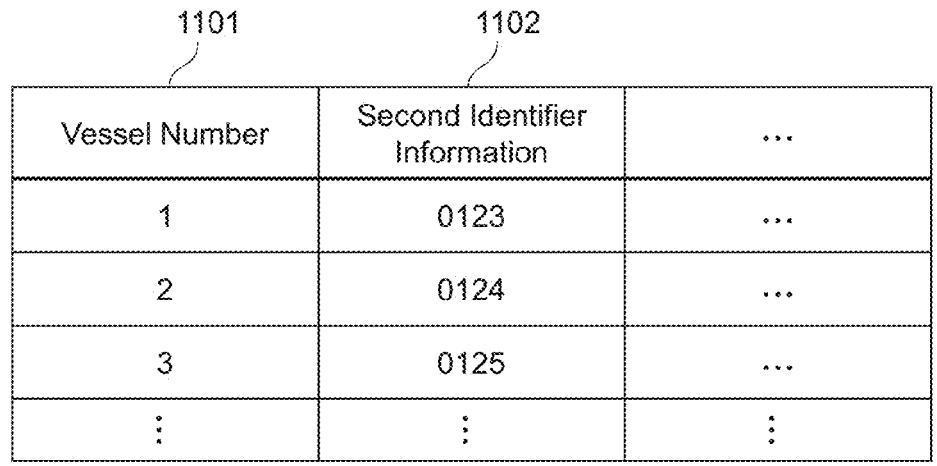
FIG. 11 is a schematic diagram showing an embodiment of a second identifier correspondence table of the present invention.
FIG. 12 is a schematic diagram showing an embodiment of an image database of the present invention.

FIG. 11 shows an example of the second identifier correspondence table 143. The second identifier correspondence table 143 contains at least a vessel number 1101 and second identifier information 1102 as the constituent items. With this table, each cell culture vessel 100 can be identified from the second identifier 102 provided to the cell culture vessel 100. It should be noted that when the second identifier 102 directly represents information that uniquely indicates a cell culture vessel, such as a vessel number, the second identifier correspondence table 143 may be omitted.

FIG. 12 shows an example of the image database 144. The image database 144 has stored therein enlarged sample images acquired from the image acquisition device 110 and a variety of pieces of information associated with the images. The image database 144 contains an image ID 1201, a vessel number 1202, a well ID 1203, and image data 1204 as the constituent items. As described above, in the image database 144, each image data 1204, the vessel number 1202, and the well ID 1203 are associated with one another.

Therefore, it is possible to manage information about which microwell's enlarged sample image as well as which treatment date of which patient corresponds to each image data 1204 by referring to the image database 144 and the sample information database 141. Although the image database 144 is created in this embodiment, it is also possible to provide the sample information database 141 with an item in which files of enlarged sample images can be registered so that enlarged sample images are registered in the sample information database 141.

The sample image management device 130 includes a contour extraction processing unit 151, a pattern detection processing unit 152, an image correction processing unit 153, a first identifier recognition processing unit 154, a database creation processing unit 155, and a second identifier recognition processing unit 156. The sample image management device 130 analyzes an enlarged sample image captured with the image acquisition device 110 using such processing units 151 to 156, and associates the enlarged sample image with the well ID based on the variety of tables described above. Accordingly, it becomes possible to uniquely identify sample information with respect to the enlarged sample image.

In this embodiment, each of the processing units 151 to 156 of the sample image management device 130 may also be implemented as the function of a program executed on a computer. That is, each of the processing units 151 to 156 may be stored as a program code in a memory on that each of the processing units 151 to 156 is implemented through execution of each program code by a CPU. Hereinafter, each of the processing units 151 to 156 will be described.

Figure 13:
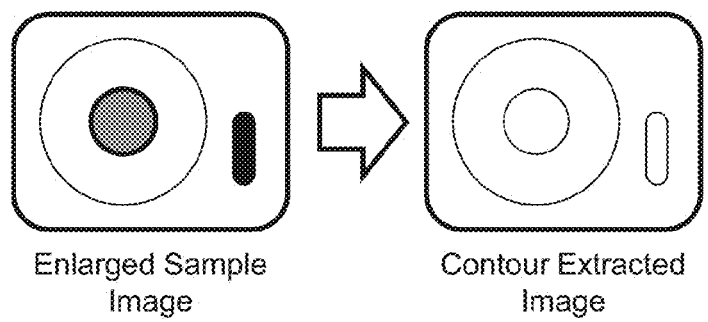
FIG. 13 is a conceptual view illustrating a process of an embodiment of a contour extraction processing unit of the present invention.

The contour extraction processing unit 151 receives an enlarged sample image, which includes a cell in the microwell 105 of the cell culture vessel 100 and the first identifier 101, from the image acquisition device 110, and executes a contour extraction process on the enlarged sample image. As the contour extraction process, a technique known to those skilled in the art can be applied. Examples of the contour extraction process include a process of executing a binarization process for converting an enlarged sample image into a two-grayscale image of black and white, and extracting a contour from the binarized image. It is also possible to, as a target to be observed is usually transparent and thus is difficult to have a gray scale at the boundary, perform differentiation on changes in the pixel values before executing a process of converting an image into a two-grayscale image. As other contour extraction processes, it is also possible to use the technique described in JP 2011-192109 A. In this document, a reference profile and a candidate profile are created, and the degree of similarity that indicates the similarity between the reference profile and the candidate profile is calculated to determine the contour of an embryo. Such a technique may be applied to the determination of the contour of a microwell and the contour of a first identifier. The contour extraction processing unit 151 extracts the contour of a figure that is formed by the outer rim (hereinafter referred to as an "outer contour") of the opening of a microwell 105, and the contour of a figure that is formed by the first identifier 101, and outputs a contour extracted image (FIG. 13).

In the sample image management device 130, an interpolation process and/or a region defining process may also be executed after the contour extraction process of the contour extraction processing unit 151. An interpolation process is a process of estimating and interpolating missing portions of a contour by combining a pattern, which is prepared in advance, with a contour extracted image. For example, when only a contour extraction process is performed, there may be cases where the outer contour of the microwell 105 and/or the contour of a figure formed by the first identifier 101 have missing portions. Therefore, a pattern of the shape of the microwell 105 and a pattern of the shape of the first identifier 101 are registered in advance so that such patterns are laid over a contour extracted image to interpolate missing portions of the contours. A region defining process is a process of defining a region surrounded by a contour. For example, when a contour on a contour extracted image has missing portions, a region that is defined by a new contour that is obtained after a contour interpolating process is defined. Performing such a region defining process can determine the range in which the following pattern matching should be performed, the dimensions of a region surrounded by the contour, or a region for calculating the area.

The pattern detection processing unit 152 executes a pattern detection process on the contour extracted image. Herein, a pattern detection process is a process of detecting which contour in the contour extracted image is the outer contour of the microwell 105 and also detecting which contour is the contour of the first identifier 101. As the pattern detection process, techniques known to those skilled in the art can be applied. As an example, there is known a method of storing templates of the shapes of the microwells 105 and templates of the shapes of the first identifiers 101 in the sample image management device 130 in advance, and performing pattern matching using the templates. The pattern detection processing unit 152 detects as the contour of the microwell 105 or the contour of the first identifier 101 a portion that has a degree of similarity greater than or equal to a predetermined degree of similarity to each template. It should be noted that the template may be enlarged or shrunk in accordance with the magnification of the image acquisition device 110, or pattern matching may be performed with a template that is being rotated.

The process of detecting the outer contour of the microwell 105 and the contour of the first identifier 101 from the contour extracted image is not limited thereto, and other methods can also be used. For example, detection may be performed using the design information on the microwells 105 and the design information on the first identifiers 101 in the well design information 142. For example, it is possible to identify the outer contour of the microwell 105 and the contour of the first identifier 101 by comparing information, such as a dimension or an area, of a figure formed by a contour on the contour extracted image with the deign information on the microwell 105 and the design information on the first identifier 101.

Figure 14:
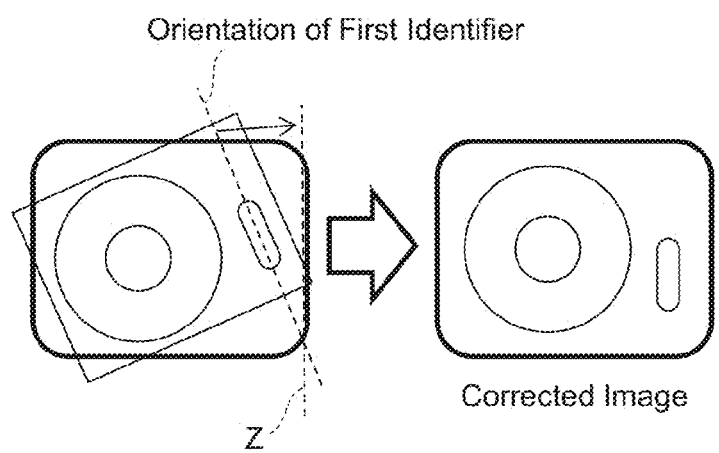
FIG. 14 is a conceptual view illustrating a process of an embodiment of an image correction processing unit of the present invention.

The image correction processing unit 153 first detects the orientation of the first identifier 101 detected by the pattern detection processing unit 152. When the first identifier 101 is a line (bar) shown in FIGS. 6 and 7, the image correction processing unit 153 may detect as a straight line indicating the orientation of the first identifier 101 the direction in which a straight line, which passes through the center of gravity of a figure formed by the contour of the first identifier 101 (i.e., straight line in the closed figure), becomes the longest. Needless to say, the "orientation" of the first identifier 101 may be detected in accordance with the shape of the first identifier 101, and other methods can also be used. Next, the image correction processing unit 153 calculates an angle representing the orientation of the first identifier 101. The "orientation" of the first identifier 101 is as described above. In the example herein, the image correction processing unit 153 determines that there is no tilt if the calculated angle of orientation is 90°. If there is a tilt, the image correction processing unit 153 corrects the contour extracted image by rotating it so that the orientation of the first identifier 101 becomes located at a position of 90° (i.e., the position of a dotted line Z in FIG. 14). The image correction processing unit 153 outputs the image, which has been corrected through rotation, as a corrected image (the right side of FIG. 14).

As another example, if pattern matching is performed by the pattern detection processing unit 152 with a template that is being rotated, it is possible to determine the angle of rotation of a template with the highest degree of similarity as the orientation of the first identifier, and create a corrected image based on the angle of rotation.

Further, as another example, rotation correction can also be performed when the first identifiers 101 are provided only to the right side, only to the left side, only to the upper side, or only to the lower side of the microwells 105. For example, when the well design information 142 has stored therein information that indicates that the first identifiers 101 are provided to the right side of the microwells 105, the image correction processing unit 153 may determine the angle of rotation that allows the first identifiers 101 to be located in the range of the right side of the microwells 105 in all of the captured enlarged images, and correct the contour extracted image by rotating it based on such angle of rotation.

It should be noted that as described above, if imaging is performed with the orientation of the cell culture vessel 100 held constant (i.e., when the third identifier 107 is provided to the cell culture vessel 100 to set the orientation of the cell culture vessel 100 to be always constant, or when the cell culture vessel 100 has a shape that can identify the orientation of the cell culture vessel), the process of the image correction processing unit 153 may be omitted.

Figure 15:
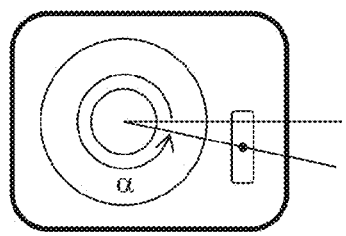
FIG. 15 is a conceptual view illustrating a process of an embodiment of a first identifier recognition processing unit of the present invention.

The first identifier recognition processing unit 154 executes a process of recognizing the first identifier 101 on a corrected image or on a contour extracted image if a corrected image has not been created. The first identifier recognition processing unit 154 calculates the angle α of the first identifier 101 with respect to the microwell (FIG. 15). When the first identifier 101 is a line (bar), the first identifier recognition processing unit 154 may calculate the angle α and/or the length of the line (bar). Thereafter, the first identifier recognition processing unit 154 refers to the first identifier correspondence table using the calculated angle α, and outputs a well ID corresponding to the calculated angle α.

Figure 16:
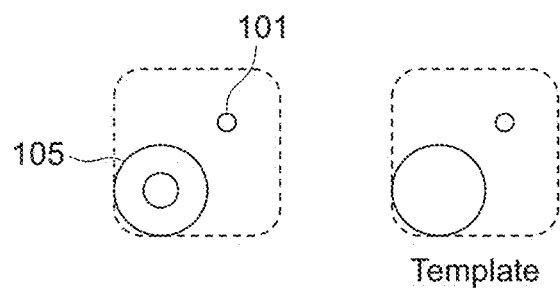
FIG. 16 is a conceptual view illustrating a process of an embodiment of a first identifier recognition processing unit of the present invention.

It should be noted that the process of the first identifier recognition processing unit 154 is not limited thereto, and other methods may also be used. In the process of the first identifier recognition processing unit 154, it is acceptable as long as a first identifier can be associated with a well ID from the relative positional relationship between the microwell 105 and the first identifier 101. It is also possible to, as shown in FIG. 16, perform template matching by preparing a plurality of templates each including a microwell and a first identifier. An enlarged sample image can be associated with a well ID from the results of template matching as long as each template and the well ID are associated with one another in the first identifier corresponding table.

Although the processing units for recognizing the first identifier 101 have been described above, a variety of combinations of the aforementioned processes is possible, and such a variety of combinations is included in the present invention. For example, the following combinations are possible:

(1) A combination of a contour extraction process, an interpolation process, a region defining process, and a first identifier recognition process based on pattern matching; and (2) A combination of a contour e action process, an interpolation process, a region defining process, a pattern detection process (i.e., pattern matching for each contour or calculation of the area/dimensions of each contour), and a first identifier recognition process (i.e., calculation of the angle α and/or the length of a line (bar)).

The contour extraction process is not necessarily required, and it is also possible to prepare a template that is close to an enlarged sample image obtained with the image acquisition device 110, such as a microscope, and execute a pattern matching process between the template and the enlarged sample image (i.e., image before subjected to a contour extraction process).

The second identifier recognition processing unit 156 refers to the second identifier correspondence table 143 based on information on the second identifier 102 read by the second identifier reading device 120, and outputs a vessel number corresponding to the information. Other than such a method, it is also possible to use a method of recognizing a vessel number using another method in advance, and read the second identifier 102 using the second identifier reading device 120 to check if the recognition is correct or not.

The database creation processing unit 155 stores the well ID output from the first identifier recognition processing unit 154, the vessel number output from the second identifier recognition processing unit 156, and the enlarged sample image in the image database 144 in association with one another.

Although a process performed on an enlarged sample image, which includes a pair of the microwell 105 and the first identifier 101, has been describe above, the present invention is not limited thereto. A similar process can be applied even when an enlarged sample image includes a plurality of pairs each having the microwell 105 and the first identifier 101 as the observed field of view contains a plurality of microwells 105. In such a case, it is acceptable as long as, after a pattern detection process, a process of cutting out each pair of the microwell 105 and the first identifier 101 is performed using the well design information 142, such as the pitch between the microwells 105, and the above-mentioned subsequent processes are executed on the cut-out image.

Figure 17:
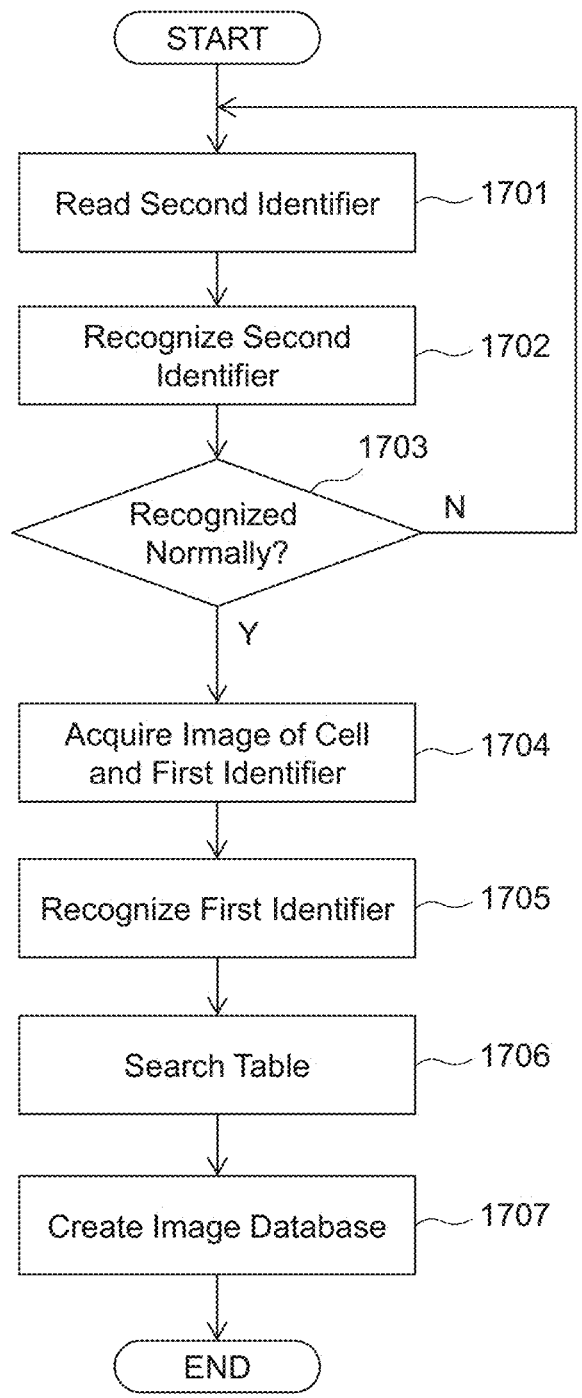
FIG. 17 is a flowchart illustrating a process flow of an embodiment of a sample image management device of the present invention.

Next, a process flow of the sample image management device 130 will be described. FIG. 17 is a flowchart illustrating a process flow of the sample image management system 1. Hereinafter, a case where the first identifiers 101 are lines (bars) will be described. It should be noted that the following process may be executed each time an image is taken into the sample image management device 130, or it is also possible to, after a plurality of images are taken into the sample image management device 130, execute the following process once on the images.

First, the second identifier reading device 120 reads the second identifier 102 of the cell culture vessel 100 (1701). Next, the second identifier recognition processing unit 156 of the sample image management device 130 refers to the second identifier correspondence table 143 using the read information on the second identifier 102. Then, the second identifier recognition processing unit 156 outputs a vessel number corresponding to the second identifier 102, and records information on the vessel number once on the storage device or the like (1702). When the second identifier 102 is not recognized normally due to an error in reading of the second identifier 102 and the like (N in 1703), the flow returns to step 1701. Although the procedures of initially recognizing the second identifier 102 are shown herein, the present invention is not limited thereto. The processes in steps 1701 to 1702 may be executed at any time point before the creation of the image database 144 in step 1707.

Next, an operator of the sample image management device 130 operates the image acquisition device 110 using the input unit 132 acquire an enlarged sample image including a cell in the microwell 105 and the first identifier 101 (1704). In this embodiment, the conditions (i.e., magnification) of the image acquisition device 110 and the image acquisition position are specified via the input unit 132, and an image captured by the image acquisition device 110 is displayed on the output unit 133 of the sample image management device 130. In the operation of acquiring an enlarged sample image, the operator instructs the sample image management device 130 to take in an image using the input unit 132 while viewing a sample image displayed on the output unit 133. It is also possible to provide the image acquisition device 110 with some input means so that the operator can take in an image using the input means while looking into the image acquisition device 110 (e.g., microscope). It should be noted that the sample image management device 130 need not necessarily operate in conjunction with the image acquisition device 110, and the advantageous effects of the present invention can be obtained as long as at least an enlarged sample image is input to the sample image management device 130.

Figure 18:
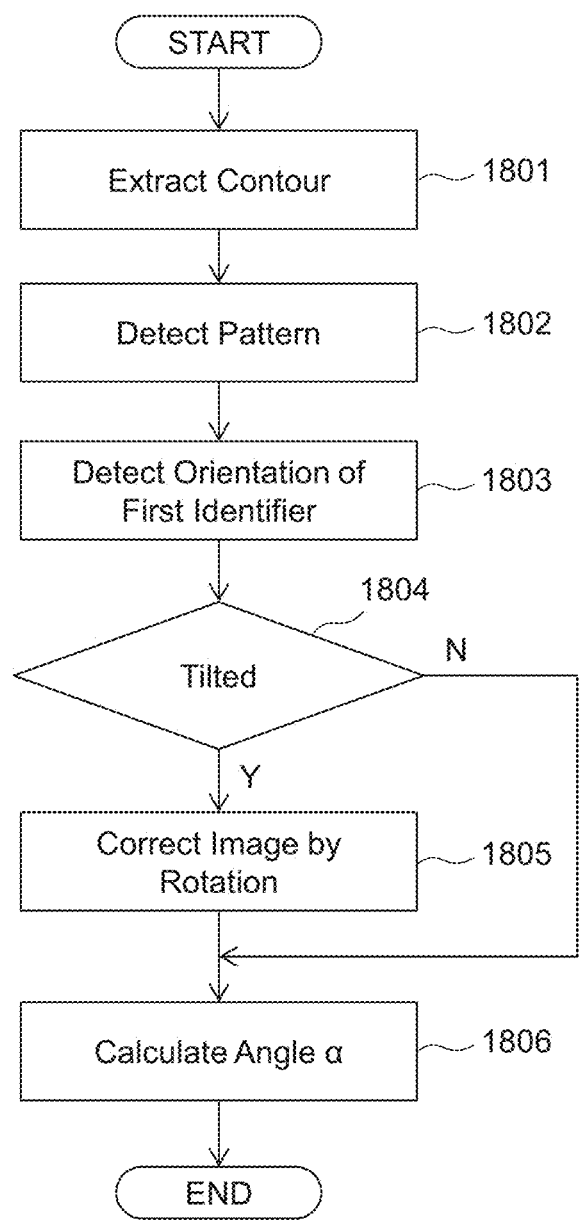
FIG. 18 is a flowchart illustrating a process flow of an embodiment of a sample image management device of the present invention.

Next, a first identifier recognition process is executed (1705). FIG. 18 is a flowchart illustrating a specific process flow in step 1705. First, the contour extraction processing unit 151 extracts a contour from an enlarged sample image including a cell and a first identifier, thereby creating a contour extracted image (1801). Next, the pattern detection processing unit 152 detects the contour of the microwell 105 and the contour of the first identifier 101 from the contour extracted image (1802).

Next, the image correction processing unit 153 detects the orientation of the first identifier 101 detected by the pattern detection processing unit 152 (1803). The image correction processing unit 153 determines the tilt of the first identifier 101 based on the angle representing the orientation of the first identifier 101. If the first identifier 101 is not tilted, the flow proceeds to step 1806 (N in 1804).

Meanwhile, if it is determined that the first identifier 101 is tilted (Y in 1804), the flow proceeds to step 1805. Next, the image correction processing unit 153 rotates the contour extracted image based on the angle representing the orientation of the first identifier 101, thereby creating a corrected image (1805).

Next, the first identifier recognition processing unit 154 executes a process of recognizing the first identifier 101 on the corrected image or on the contour extracted image if the correct image has not been created. The first identifier recognition processing unit 154 calculates the angle α of the first identifier with respect to the microwell (1806). Upon completion of such processes, the flow proceeds to step 1706 in FIG. 17.

Next, the first identifier recognition processing unit 154 searches the first identifier correspondence table using the calculated angle α (1706). The first identifier recognition processing unit 154 once stores information on the well ID corresponding to the calculated angle α into the storage device or the like. It should be noted that information, such as a well ID, may be displayed on the output unit 133 at this time point so that the operator can confirm the results of recognition.

Next, the database creation processing unit 155 stores the well ID output from the first identifier recognition processing unit 154, the vessel number output from the second identifier recognition processing unit 156, and the enlarged sample image in the image database 144 in association with one another (1707).

As described above, according to this embodiment, a well ID is automatically associated with an enlarged sample image. Thus, it is possible to eliminate the cumbersome task of manually associating sample information with an enlarged sample image, and further reduce the possibility of errors that may occur in the manual association process. Further, it is also possible to associate not only a well ID but also a vessel number with an enlarged sample image, and uniquely identify all pieces of sample information with respect to an enlarged sample image.

It should be noted that the present invention is not limited to the aforementioned embodiments, and includes a variety of variations. For example, although the aforementioned embodiments have been described in detail to clearly illustrate the present invention, the present invention need not include all of the configurations described in the embodiments. It is possible to replace a part of a configuration of an embodiment with a configuration of another embodiment. In addition, it is also possible to add, to a configuration of an embodiment, a configuration of another embodiment. Further, it is also possible to, for a part of a configuration of each embodiment, add, remove, or substitute a configuration of another embodiment.

In addition, as described above, each processing unit of the sample image management device 130 may be implemented by a program code of software that implements the function of the embodiment. In such a case, a storage medium having recorded thereon a program code is provided to an information processing device, and the information processing device (or a CPU) reads the program code stored in the storage medium. In this case, the program code itself read from the storage medium implements the function of the aforementioned embodiment, and the program code itself and the storage medium having recorded thereon the program code constitute the present invention. A storage medium described herein is a variety of types of non-transitory computer readable media. As a non-transitory computer readable medium for supplying such a program code, for example, a flexible disk, CD-ROM, DVD-ROM, a hard disk, an optical disc, a magneto-optical disc, CD-R, a magnetic tape, a nonvolatile memory card, ROM, or the like is used.

In addition, the information lines in the drawings represent those that are considered to be necessary for the description, and do not necessarily represent all information lines that are necessary for a product. Thus, in practice, almost all structures may be considered to be mutually connected.

REFERENCE SIGNS LIST

Sample image management system
100 Cell culture vessel
101 First identifier
102 Second identifier
103 Bottom
104 Sidewall
105 Microwell
106 Cell storage part
107 Third identifier
110 Image acquisition device
120 Second identifier reading device
130 Sample image management device
131 Storage device
132 Input unit
133 Output unit
141 Sample information database
142 Well design information
143 Second identifier correspondence table
144 Image database
151 Contour extraction processing unit
152 Pattern detection processing unit
153 Image correction processing unit
154 First identifier recognition processing unit
155 Database creation processing unit
156 Second identifier recognition processing unit
r Opening width of cell culture vessel
R Opening width of microwell
a Pitch between microwells
α Angle of first identifier with respect to microwell

The invention claimed is:

1. A sample image management system comprising:
a storage unit that stores first information, the first information including position information on each microwell of a plurality of microwells arranged on bottom of a cell culture vessel, and information on each first identifier provided to each microwell in pairs; and
a sample image management unit that analyzes, in an enlarged sample image including a pair of the first identifier and the microwell, the microwell and the first identifier, and associates position information on the microwell in the first information with the enlarged sample image on the basis of the first information.

2. The sample image management system according to claim 1,
wherein:
the sample image management unit associates a second identifier read from the cell culture vessel and the position information on the microwell in the first information with the enlarged sample image.

3. The sample image management system according to claim 1,
wherein:
the sample image management unit, in analyzing the microwell and the first identifier in the enlarged sample image, extracts an outer contour of the microwell and a contour of the first identifier in the enlarged sample image.

4. The sample image management system according to claim 1,
wherein:
the sample image management unit, in analyzing the microwell and the first identifier in the enlarged sample image, analyzes an orientation of the first identifier in the enlarged sample image, and corrects the enlarged sample image by rotating the enlarged sample image.

5. The sample image management system according to claim 1,
wherein:
the information on the first identifier in the first information includes information on a relative position of the first identifier with respect to its paired microwell, and information held by the first identifier, and
the sample image management unit, in analyzing the microwell and the first identifier in the enlarged sample image, recognizes the relative position of the first identifier with respect to its paired microwell, and the information held by the first identifier in the enlarged sample image.

6. A non-transitory computer readable media storing a program for causing an information processing device, which includes a processor and a storage unit, to execute a sample image management process for a cell culture vessel that includes a plurality of microwells and a plurality of first identifiers provided to the respective microwells in pairs, the program causing the processor to execute:
- a process of analyzing, in an enlarged sample image including a pair of the first identifier and the microwell, the microwell and the first identifier; and
- a process of associating, on the basis of first information, which includes position information on the microwell and information on the first identifier that are associated with one another, the position information on the microwell in the first information with the enlarged sample image.

7. The non-transitory computer readable media according to claim 6,
wherein:
the program further causing the processor to execute a process of associating a second identifier read from the cell culture vessel and the position information on the microwell in the first information with the enlarged sample image.

8. The non-transitory computer readable media according to claim 6,
wherein:
the analyzing process includes extracting an outer contour of the microwell and a contour of the first identifier in the enlarged sample image.

9. The non-transitory computer readable media according to claim 6,
wherein:
the analyzing process includes analyzing an orientation of the first identifier in the enlarged sample image and correcting the enlarged sample image by rotating the enlarged sample image.

10. The non-transitory computer readable media according to claim 6,
wherein:
the information on the first identifier in the first information includes information on a relative position of the first identifier with respect to its paired microwell, and information held by the first identifier, and
the analyzing process includes recognizing the relative position of the first identifier with respect to its paired microwell, and the information held by the first identifier in the enlarged sample image.

11. A sample image management method for a cell culture vessel that includes a plurality of microwells and a plurality of first identifiers provided to the respective microwells in pairs, the method comprising:
- analyzing, in an enlarged sample image including a pair of the first identifier and the microwell, the microwell and the first identifier; and
- associating, on the basis of first information, which includes position information on the microwell and information on the first identifier that are associated with one another, the position information on the microwell in the first information with the enlarged sample image.

12. The sample image management method according to claim 11, further comprising:
associating a second identifier read from the cell culture vessel and the position information on the microwell in the first information with the enlarged sample image.

13. The sample image management method according to claim 11, wherein the analyzing includes extracting an outer contour of the microwell and a contour of the first identifier in the enlarged sample image.

14. The sample image management method according to claim 11, wherein the analyzing includes analyzing an orientation of the first identifier in the enlarged sample image and correcting the enlarged sample image by rotating the enlarged sample image.

15. The sample image management method according to claim 11, wherein:
the information on the first identifier in the first information includes at least one of information on a relative position of the first identifier with respect to its paired microwell, and information held by the first identifier, and
the analyzing includes recognizing at least one of the relative position of the first identifier with respect to its paired microwell, and the information held by the first identifier in the enlarged sample image.

* * * * *